United States Patent
Lange et al.

(10) Patent No.: US 7,295,650 B2
(45) Date of Patent: Nov. 13, 2007

(54) METHOD FOR OPERATING A PRIMARY BEAM STOP

(75) Inventors: Joachim Lange, Hagenbach (DE); Rolf-Dieter Schipper, Karlsruhe (DE)

(73) Assignee: Bruker AXS GmbH, Karlsruhe (DE)

( * ) Notice: Subject to any disclaimer, the term of this patent is extended or adjusted under 35 U.S.C. 154(b) by 0 days.

(21) Appl. No.: 11/522,382

(22) Filed: Sep. 18, 2006

(65) Prior Publication Data
US 2007/0007464 A1 Jan. 11, 2007

Related U.S. Application Data

(62) Division of application No. 10/810,820, filed on Mar. 29, 2004, now abandoned.

(30) Foreign Application Priority Data
Apr. 17, 2003 (DE) ................ 103 17 677

(51) Int. Cl.
*G01T 3/00* (2006.01)
*G01N 23/201* (2006.01)
(52) U.S. Cl. .............. 378/86; 378/70; 378/87; 378/90; 250/390.01; 250/390.1
(58) Field of Classification Search ......... 250/390.01, 250/390.1; 378/70, 86, 87, 90
See application file for complete search history.

(56) References Cited

U.S. PATENT DOCUMENTS

| 6,163,592 | A  | * | 12/2000 | He et al. ................. | 378/71 |
| 7,139,366 | B1 | * | 11/2006 | Jiang ...................... | 378/88 |
| 2003/0219099 | A1 | * | 11/2003 | He et al. ................. | 378/70 |

* cited by examiner

*Primary Examiner*—David Porta
*Assistant Examiner*—Casey Bryant
(74) *Attorney, Agent, or Firm*—Paul Vincent

(57) ABSTRACT

A method for operating an X-ray or neutron-optical system and beam stop comprising an X-ray or neutron source (1) from which corresponding radiation is guided as a primary beam (2) to a sample (4) under investigation, with an X-ray or neutron detector (6) for receiving radiation diffracted or scattered from the sample (4), wherein the source (1), the sample and the detector are disposed substantially on one line (=z-axis) and wherein a beam stop (5; 31; 41) is provided between the sample and the detector whose cross-sectional shape is adjusted to the cross-section of the primary beam is characterized in that the beam stop is disposed to be displaceable along the z-direction for optimum adjustment of the amounts of useful and interfering radiation impinging on the detector. This protects the detector from the influence of the primary beam while allowing a maximum amount of diffracted or scattered radiation to reach the detector, wherein the beam stop can be easily adjusted to temporally changing properties of the beam optics.

9 Claims, 4 Drawing Sheets

METHOD FOR OPERATING A PRIMARY BEAM STOP

This application is a divisional of Ser. No. 10/810,820 filed on Mar. 29, 2004 now abandoned and also claims Paris Convention priority of DE 103 17 677.2 filed Apr. 17, 2003 the complete disclosure of which is hereby incorporated by reference.

BACKGROUND OF THE INVENTION

The invention concerns a method for operating an X-ray or neutron-optical system with an X-ray or neutron source from which associated radiation is guided as a primary beam to a sample under investigation, and with an X-ray or neutron detector for receiving radiation diffracted or scattered from the sample, wherein the source, the sample and the detector are substantially disposed on one line (=z-axis), and wherein a beam stop is provided between the sample and the detector, whose cross-sectional shape is adjusted, perpendicularly to the z-direction, to the cross-section of the primary beam.

An X-ray optical system of this type is disclosed e.g. in the company document "HR-PHK for NanoSTAR" Instruction Handbook, Anton Paar GmbH, Kärntner Str. 322, A-8054 Graz (Austria), 1998, in particular, on page 16.

X-ray and neutron-optical methods are used to investigate the properties, i.e. material properties, of samples. Towards this end, a focussed X-ray or neutron beam is directed onto the sample where it interacts with the sample in a plurality of ways, in particular through scattering and/or diffraction. The X-ray or neutron radiation after the interaction process is registered by a detector and subsequently evaluated to obtain information about the properties of the sample.

In many of these methods, only a small part of the X-ray or neutron radiation is deflected in direction; the major portion of the radiation passes the sample without deflection. The non-deflected part of the radiation is called the primary beam, both in front of as well as behind the sample. Detectors for registering diffracted or scattered radiation must usually be protected from direct influence of the primary beam to prevent irreversible damage to the detector. Towards this end, so-called beam stops are used which partially shield the detector to prevent impingement of primary radiation. A beam stop can also shield disturbing divergent parasitic radiation (e.g. through Fresnel diffraction on collimator edges).

A conventional beam stop is described in the company document of Anton Paar GmbH loc. cit. The beam stop consists essentially of a gold plate which is fixed in a steel ring using nylon threads. The position of the gold plate in the annular plane (xy plane) can be adjusted with two micrometer screws. The steel ring is flanged to the detector.

The shape of the primary beam, in particular its diameter, depends on various factors. First of all, the components used such as diaphragms or the beam optics have production tolerances. Secondly, there are temporally varying properties of the beam optics, such as e.g. temperature influences, aging effects, or varying experimental structures.

To provide sufficient and reliable protection of the detector under these circumstances, a relatively large beam stop must be used which also shields part of the radiation in the region of small angle scattering (approximately 0.1 to 5° beam deflection), and information about the sample can be lost. Alternatively, the beam stop can be iteratively adjusted to a given beam optics. In this case, varying properties of the beam optics cannot be corrected.

In contrast thereto, it is the underlying purpose of the present invention to provide a method for operating a beam stop which protects the detector from the influence of the primary beam and divergent parasitic interfering radiation and at the same time permits passage of a maximum selectable part of diffracted or scattered radiation to the detector, wherein the beam stop can be easily adjusted to temporally varying properties of the beam optics.

SUMMARY OF THE INVENTION

This object is achieved in a surprisingly simple but effective fashion with a method for operating an X-ray or neutron optical system and beam stop of the above-mentioned type in that the beam stop is disposed to be displaceable along the z-direction to optimally set the ratio of useful radiation to interfering radiation reaching the detector, as further defined in the independent method claim.

After penetration through the sample, the primary beam is generally divergent, i.e. the beam diameter increases with the propagation path along the beam axis (z-axis). The inventive feature that the beam stop can be displaced in the z-direction, i.e. towards the detector or away from the detector, permits displacement of the beam stop to exactly that position along the beam path, where the fixed diameter of the beam stop and the spatially varying diameter of the primary beam (and of the parasitic stray radiation) coincide. This geometry keeps the primary beam and parasitic stray radiation away from the detector and at the same time diffraction phenomenon close to the beam can be largely detected by the detector.

In other words, in accordance with the invention, the diameter of the shielding projection of the beam stop in the detector plane (perpendicular to the beam axis, z-direction) can be set as desired. When the shadow cast by the beam stop exactly covers the beam spot of the primary beam and optionally parasitic radiation at the detector plane, the position of the beam stop is optimum. The diameter of the shielding projection can be adjusted to the experimental conditions, in particular to the exact dimensions of the components. Change of the shielding projection is easy to adjust in response to time-dependent changes of the properties of the beam optics.

In a particularly preferred embodiment of the inventive method, the system is adjusted to measure small-angle scattering, in particular between 0.1° and 5°. In this case, exact blanking of the interfering radiation of the primary beam and divergent parasitic radiation is particularly advantageous to guarantee maximum information content of the detected useful radiation, since the useful radiation of small-angle scattering experiments is mainly radiation diffracted close to the beam.

In a preferred embodiment, the beam stop can be adjusted in an xy-plane, perpendicular to the z-direction which permits setting of the diameter and also of the position of the shielding projection of the beam stop at the detector plane.

In one additional advantageous embodiment, the beam stop has a round, preferably circular cross-section. The cross-sections of the primary beam and parasitic stray radiation are also round such that in this case, the cross-section of the beam stop has a shape adapted to the standard situation.

One embodiment of an inventive method is also preferred, with which the beam stop has a shape similar to a truncated cone. The cone axis is thereby oriented on the beam axis and the broader truncated cone side faces the source or the sample. In this case, the broad truncated cone side edge defines a precise border of the shadowed region in the path of rays. Interaction between radiation and the cone surface is largely eliminated.

In a further advantageous embodiment of the inventive method, the beam stop is formed from a material having good radiation-absorbing properties, in particular from Au and/or Sb and/or Pb and/or W and/or Bi. In this case, the beam stop may be relatively thin and light, which facilitates its adjustment.

One embodiment is also advantageous with which the beam stop can be displaced in the z-direction by a motor to permit highly precise mechanical adjustment in the z-direction.

In one particularly preferred further development of this embodiment, the system can be automatically adjusted in accordance with predetermined criteria. Automatic adjustment is possible, in particular, after each change of the experimental structure or before each measurement. The measurements are carried out under optimum conditions. Typical criteria are e.g. keeping below a certain upper power limit for radiation on the detector.

One embodiment of the inventive method is also preferred with which the surface of the beam stop facing the impinging beam is concave. The radiation impinges approximately perpendicularly to the surface of the beam stop, achieving good radiation absorption.

In another preferred embodiment, the detector is a one-element detector (zero-dimension detector) which can scan a defined angle region about the z-axis. One-element detectors are particularly inexpensive and reliable.

In an alternative embodiment, the detector is a one-dimensional detector which can increase the measuring speed for measuring an angular or solid angular region.

In a further, particularly preferred alternative embodiment having even larger measuring speeds for measuring a solid angle region, the detector is a two-dimensional area detector, wherein the detector surface is disposed substantially perpendicular to the z-direction. Area detectors are particularly sensitive.

Further advantages of the invention can be extracted from the description and the drawing. The features mentioned above and below can be used in accordance with the invention individually or collectively in arbitrary combination. The embodiments shown and described are not to be understood as exhaustive enumeration but have exemplary character for describing the invention.

The inventive method is illustrated in the drawing and is explained in more detail with reference to embodiments.

DESCRIPTION OF THE PREFERRED EMBODIMENT

Figure 1:
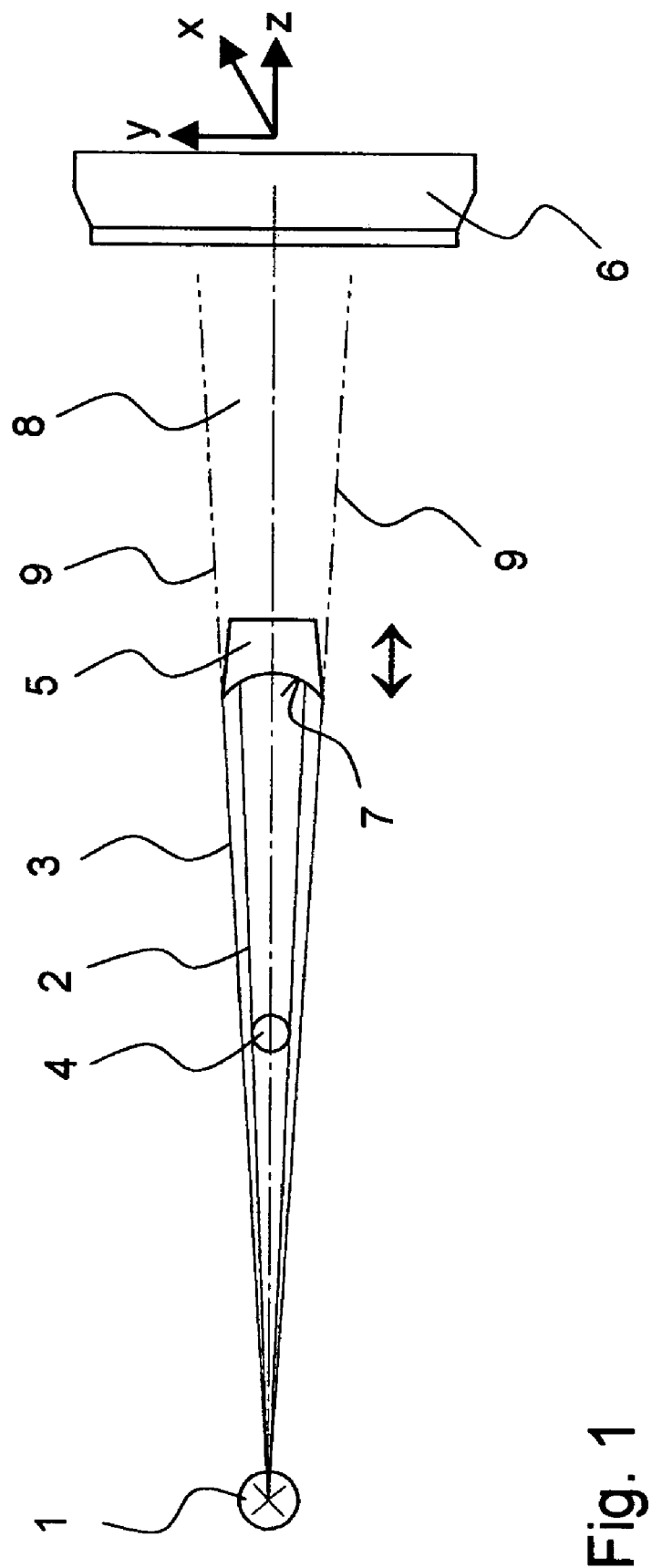
FIG. 1 shows the schematic path of rays of one embodiment of an inventive system with the beam stop adjusted in the z-direction.

FIG. 1 shows the beam path of one embodiment of the inventive method for operating an X-ray or neutron-optical system. A source 1, which is shown highly schematically, emits radiation (X-ray or neutron radiation) along a z-axis. The emitted radiation is divergent (or convergent) i.e. its cross-section increases (or decreases) with increasing propagation in the positive z-direction. The radiation consists substantially of a conical primary beam 2 whose external edge region is surrounded by a conical surface of parasitic interfering radiation 3. The interfering radiation 3 can be produced e.g. through diffraction effects on collimators associated with the source 1. The source 1 denotes the device which generates the primary beam 2 impinging on the sample, i.e. a last mirror, a last diaphragm, or a last collimator behind an X-ray tube or a neutron emitter (which is often radioactive).

A sample 4 is disposed on the beam axis (z-axis) of the primary beam 2 and can be completely illuminated by the primary beam. A major part of the primary beam 2 penetrates the sample 4 without being changed, while another part of the radiation interacts with the sample 4 in a manner not shown and is scattered or diffracted out of the conical surface of primary beam 2 and interfering radiation 3.

A beam stop 5 and a two-dimensional area detector 6 are also disposed on the beam axis. The beam stop 5 is disposed between sample 4 and area detector 6 and can be displaced along the z-axis. Adjustment of the position of the beam stop 5 in a xy-plane perpendicular to the z-direction is also possible. The outer edge 7 of the beam stop 5 facing the sample 4 extends perpendicular to the z-direction to the same extent as the conical surface of the interfering radiation 3 at this z-position, thereby keeping a solid angular region 8, which is delimited by edges 9, free from primary beam 2 radiation and also from interfering radiation 3. The portion of the area detector 6 within the solid angular region 8 remains free from intense radiation, thereby protecting the area detector 6 from damage. The remaining surface of the area detector 6 is available to detect radiation diffracted or scattered from the sample 4.

If the beam stop were disposed further to the left, i.e. at a lower z-position closer to the sample 4, in addition to the primary radiation 2 and the interfering radiation 3, further radiation diffracted or scattered by the sample 4 would be absorbed. If however, the beam stop 5 were disposed further to the right at a larger z-position further away from the sample 4, part of the interfering radiation 3 or even of the primary beam 2 could reach the area detector 6.

Figure 2:
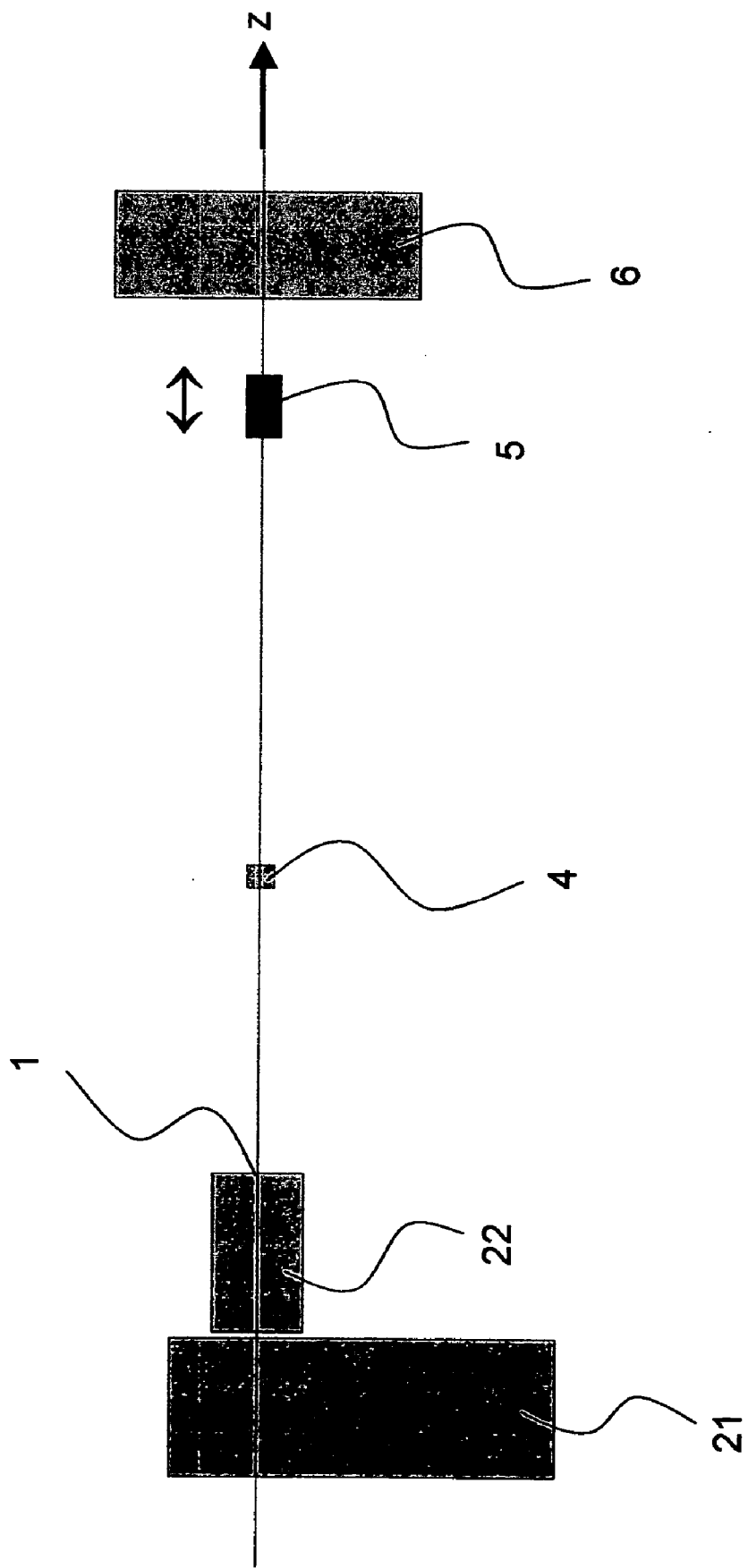
FIG. 2 shows the schematic structure of an embodiment of the inventive method.

FIG. 2 shows an embodiment of an X-ray optical system for use in the inventive method. An optical means 22 is connected to an X-ray tube 21 which prepares, in particular, monochromatizes and focusses the X-ray radiation provided by the X-ray tube 21. An outlet window of the optical means 22 facing the sample 4 defines the source 1 of the X-ray radiation in accordance with the invention. The source 1 emits the primary beam, and any disturbing parasitic radiation, substantially along a beam axis coinciding with the z-axis.

A beam stop 5 is disposed between the sample 4 and an area detector 6 which can be displaced and locked on the beam axis (z-axis). Displacement of the beam stop 5 can define the X-ray radiation impinging on the area detector 6 to exclude interfering radiation from being detected and to supply a maximum amount of useful radiation for detection.

Figure 3:
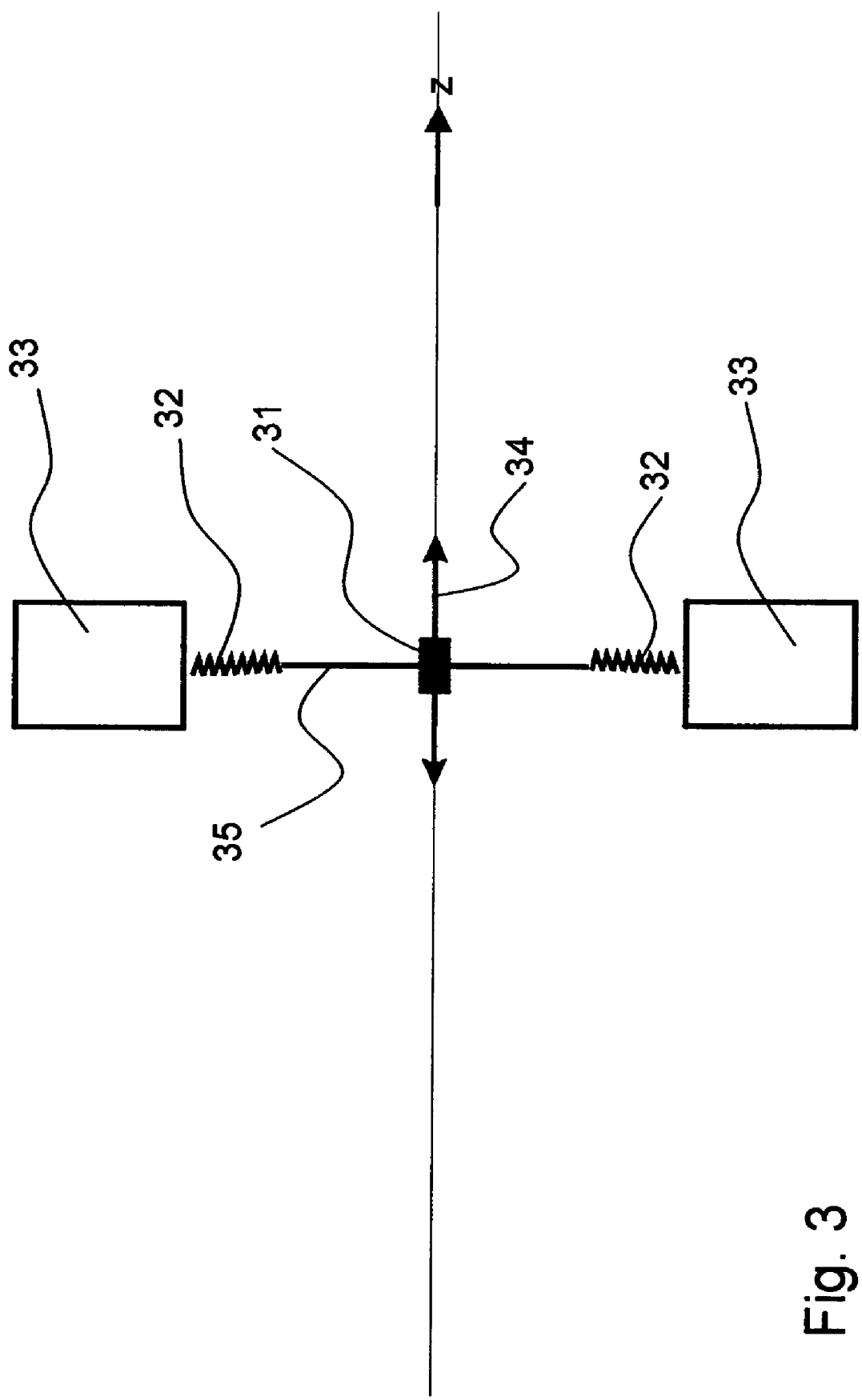
FIG. 3 shows the schematic structure of a beam stop having spring suspension, which, in accordance with the invention, can be displaced in the z-direction.

FIG. 3 shows an embodiment of a beam stop 31 within the scope of the inventive method. The beam stop 31 consists of a cylindrical permanent magnetic plate whose side facing the source is coated with gold. The plate may also comprise a massive absorbing member, e.g. of gold, lead, bismuth etc. and a permanent-magnetic element which can move the beam stop 31 in a magnetic field. The cylindrical axis and magnet axis coincide with the z-axis. The beam stop 31 is fastened, via capton threads 35, to tension springs 32 which are attached to a stationary holding frame 33.

To adjust the beam stop 31 along the z-axis, a z-dependent magnetic field or a magnetic field in the z-direction can be generated (in a manner not shown) in the region of the beam stop 31 using an electromagnetic coil thereby increasing a force on the beam stop 31. This force deflects the beam stop 31 in the direction of arrow 34. This deflection is opposed by the restoring force of the tension springs 32. In accordance with Hooke's law, the deflection of the beam stop 34 from the central position shown increases linearly with the direct current flowing through the electromagnetic coil, thereby facilitating adjustment of the z-position of the beam stop 31. The electromagnetic coil may advantageously be integrated in the holding frame 33.

Instead of a magnetic device, mechanical structures may be used for moving the beam stop 31.

To adjust the beam stop 31, in particular for testing blockage of the primary beam, a robust auxiliary detector which is not damaged by direct primary radiation can be used instead of a sensitive detector, or the radiant power of the source is reduced for the adjustment measurement such that the sensitive detector cannot be damaged. This may be effected e.g. using an absorber in the primary beam.

Figure 4:
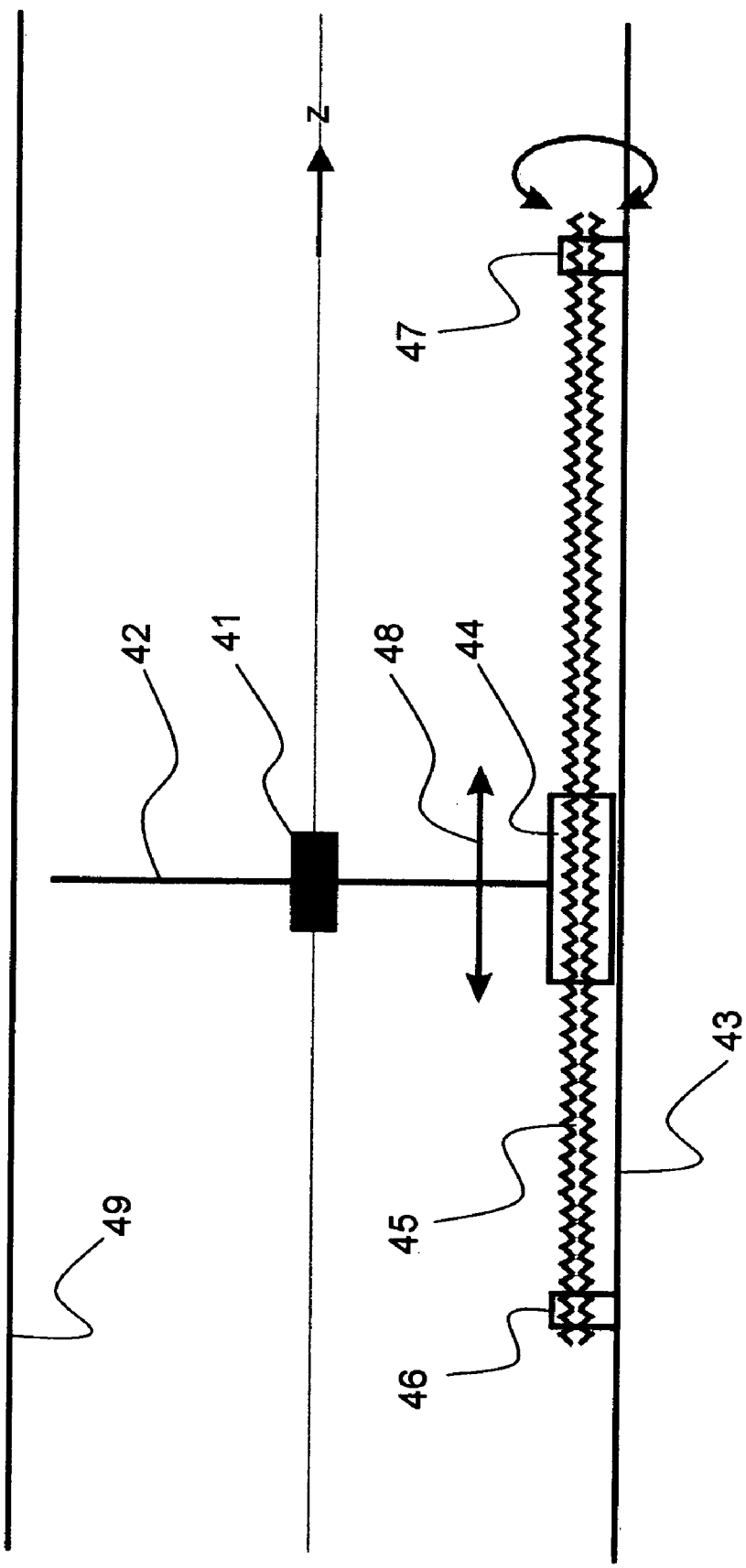
FIG. 4 shows the schematic structure of a beam stop with spindle drive, which, in accordance with the invention, can be displaced in the z-direction.

FIG. 4 shows another embodiment of a beam stop 41 within the scope of the inventive method. The beam stop 41 consists of a cylindrical plate with a cylinder axis extending along the z-axis. The beam stop 41 is disposed on a stand 42. This stand 42 is guided in a rail 43 which extends parallel to the z-axis. A foot 44 of the stand 42 has a thread in which a spindle 45 extends. This spindle 45 is mounted via jaws 46, 47 to the rail 43 and can be driven by a motor (not shown). Rotation of the spindle displaces the foot 44 along the rail 43 thereby displacing the entire stand 42 in the direction of arrow 48 to position the beam stop 41 along the z-axis. The entire arrangement with beam stop 41 is disposed within a radiation shield 49.

Beam stops which can be adjusted in all three spatial directions, can also be used to shadow or blank individual diffracted beams in a diffraction spectrum. In this way, combinations of several beam stops are possible within the scope of this invention.

We claim:

1. A method for operating an X-ray or neutron optical system, the system having an X-ray or a neutron source from which radiation is emitted as a primary beam, and impinges on a sample to be examined, and with an X-ray or neutron detector for detecting radiation refracted or scattered from the sample, wherein the source, the sample and the detector are substantially collinear to define a z-direction, wherein a beam stop is disposed between the sample and the detector, the beam stop having a cross-sectional shape, perpendicular to the z-direction, which is adapted to the cross-section of the primary beam, wherein the beam stop is disposed for displacement along the z-direction to optimize a ratio between a useful beam fraction and an interfering beam fraction impinging on the detector, the method comprising the step of:

adjusting the X-ray or neutron optical system to time changes in the properties of the beam prior to each measurement of the sample by automatically adjusting a position of the beam stop in the z-direction in such a fashion that, in a plane of the detector, a shadow cast by the beam stop precisely shields the primary beam and parasitic interfering radiation.

2. The method of claim 1, wherein the parasitic interfering beam radiation includes radiation which is refracted from collimators and collimators associated with the source.

3. The method of claim 1, wherein a position of the beam stop is also adjusted in an x-y plane, perpendicular to the z-direction.

4. The method of claim 1, wherein the beam stop is motor driven for alignment in the z-direction.

5. The method of claim 1, wherein the beam stop is configured as a permanent magnetic plate or with permanent magnetic elements, wherein a z-position of the beam stop is adjusted by means of the magnetic field of an electromagnetic coil.

6. The method of claim 1, wherein a robust auxiliary detector, which is not damaged by direct influence of the primary beam, is utilized for alignment of the beam stop, wherein a second more sensitive detector is utilized for determination of the properties of the sample.

7. The method of claim 1, wherein a beam intensity of the source is sufficiently reduced during an alignment measurement as to prevent damage to the detector.

8. The method of claim 7, wherein an absorber is disposed in the primary beam to reduce the beam intensity.

9. The method of claim 1, wherein adjustment of the X-ray or neutron optical system takes into consideration influences of temperature changes and influences and/or degradations in beam optics.

* * * * *